(12) United States Patent
Weil et al.

(10) Patent No.: US 6,171,257 B1
(45) Date of Patent: *Jan. 9, 2001

(54) METHOD AND SYSTEM FOR PREDICTING THE IMMEDIATE SUCCESS OF A DEFIBRILLATORY SHOCK DURING CARDIAC ARREST

(75) Inventors: Max Harry Weil, Northbrook, IL (US); Wanchun Tang, Palm Desert; Joe Bisera, Camarillo, both of CA (US)

(73) Assignee: The Institute of Critical Care Medicine, Palm Springs, CA (US)

( * ) Notice: Under 35 U.S.C. 154(b), the term of this patent shall be extended for 0 days.

This patent is subject to a terminal disclaimer.

(21) Appl. No.: 09/385,537

(22) Filed: Aug. 30, 1999

Related U.S. Application Data

(63) Continuation of application No. 09/160,953, filed on Sep. 25, 1998, now Pat. No. 5,957,856.

(51) Int. Cl.[7] .................................................. A61B 5/046
(52) U.S. Cl. .............................................................. 600/518
(58) Field of Search ................................. 607/5, 6, 7, 8; 600/509, 515, 518

(56) References Cited

U.S. PATENT DOCUMENTS 5,077,667 * 12/1991 Brown et al. ...................... 600/518

* cited by examiner

Primary Examiner—Scott M. Getzow
(74) Attorney, Agent, or Firm—Leon D. Rosen; Timothy Thut Tyson; Freilich Hornbaker & Rosen

(57) ABSTRACT

A method and system (30, 50) for predicting the immediate success of a defibrillatory shock during cardiac arrest are shown. The sequencing of cardiopulmonary resuscitation is determined by an electronic computer (80) based on the probability of success as determined by a comparison of the amplitude spectrum area or the power spectrum area of an electrocardiogram sample and to empirical data. When the probability of successful resuscitation is 80% or greater, immediate defibrillation is implemented. When the probability of success is 20% or less, advanced cardiopulmonary resuscitation is implemented. When the probability of success remains greater than 20% but less than 80% for a period of four minutes, the patient is also defibrillated.

2 Claims, 6 Drawing Sheets

METHOD AND SYSTEM FOR PREDICTING THE IMMEDIATE SUCCESS OF A DEFIBRILLATORY SHOCK DURING CARDIAC ARREST

CROSS REFERENCE TO RELATED APPLICATION

This is a continuation of U.S. patent application Ser. No. 09/160,953, filed Sep. 25, 1998, now U.S. Pat. No. 5,957,856 issued Sep. 28, 1999, the contents of which are incorporated herein by reference.

TECHNICAL FIELD

The present invention relates generally to the field of monitoring and treatment of heart attack and other victims who have cardiac arrest due to ventricular fibrillation, and more particularly to a method and system for determining when a victim should be defibrillated or treated with alternative therapies.

BACKGROUND ART

Ventricular fibrillation is the rapid uncoordinated fluttering contractions of the ventricles of the heart resulting in loss of synchronization between the heartbeat and pulse beat. Unless the victim is electrically defibrillated within the first two minutes of onset of the ventricular fibrillation, complementary therapy is indicated including conventional cardiopulmonary resuscitation (CPR) with compression of the chest, drug treatment, and occasionally open heart message. The use of electrical defibrillation is often dependent upon the identification of the situation by emergency personnel who work under adverse conditions and time pressures. Inappropriate timing of defibrillation is harmful because it of itself produces myocardial injury reducing the likelihood of ultimate survival.

Current resuscitation methods are constrained in part by the lack of practical and reliable real time monitors of the efficacy of electrical defibrillation interventions. This is especially pertinent to current cardiopulmonary resuscitation (CPR) practices in which precordial compression is interrupted for repetitive attempts at electrical defibrillation during hands-off intervals. When critical levels of coronary perfusion cannot be maintained, the electrical defibrillation attempt predictably fails, Niemann, J. T., et al., "Treatment of Prolonged Ventricular Fibrillation. Immediate Countershock Versus High-dose Epinephrine and CPR Preceding Countershock," *Circulation*, 85:281–287, 1992. This issue is also of practical moment with respect to programming automated external defibrillators which require even greater hands-off intervals.

Studies of human victims of cardiac arrest have previously suggested that the amplitude of ventricular fibrillation (VF) waveforms may predict the outcome of a defibrillation attempt. Significantly greater VF amplitudes are associated with correspondingly greater likelihood of restoring spontaneous circulation, Weaver, W. D., et al., "Amplitude of Ventricular Fibrillation Waveform and Outcome After Cardiac Arrest," *Annals of Internal Medicine*, 102:53–55, 1985; Stults, K. R., et al., "Ventricular Fibrillation Amplitude Predicts Ability to Defibrillate," *Journal of the American College of Cardiology*, 9:152A (abstract only), 1987; Dalzell, G. W., Adgey, A. A., "Determinants of Successful Transthoracic Defibrillation and Outcome in Ventricular Fibrillation," *British Heart Journal*, 65:311–316, 1991; and, Callaham, M., et al., "Prehospital Cardiac Arrest Treated by Urban First-responders; Profile of Patient Response and Prediction of Outcome by Ventricular Fibrillation Waveform," *Annals of Emergency Medicine*, 22:1664–1667, 1993. In addition to the ventricular fibrillation (VF) amplitude, the median frequency of VF obtained by Fourier analysis of VF waveforms serves as a predictor of the success of electrical defibrillation in swine, Brown, C. G., et al., "Median Frequency—A New Parameter for Predicting Defibrillation Success Rate," *Annals of Emergency Medicine*, 20:787–789, 1991. Also, the median frequency of VF serves as a predictor in humans, Strohmenger, H. U., et al., "Frequency of Ventricular fibrillation as Predictor of Defibrillation Success during Cardiac Surgery," *Anesthesiology Analogs*, 79:434–438, 1994. High frequency of ventricular fibrillation (VF) wavelets are associated with significantly greater success of defibrillation. The frequency of VF is also related to the duration of untreated VF, Brown, C. G., et al., "Estimating the Duration of Ventricular Fibrillation,"*Annals of Emergency Medicine*, 18:1181–1185, 1989; Dzwonczyk, R., et al., "The Median Frequency of ECG During Ventricular Fibrillation: Its Use in an Algorithm for Estimating the Duration of Cardiac Arrest," *IEEE Transactions in Biomedical Engineering*, 37:640–646, 1990; Martin, D. R., et al., "Frequency Analysis of the Human and Swine Electrocardiogram During Ventricular Fibrillation," *Resuscitation*, 22:85–91, 1991; and Brown, C. G., et al., "Physiologic Measurement of Ventricular Fibrillation ECG Signal: Estimating the Duration of Ventricular Fibrillation," *Annals of Emergency Medicine*, 22:70–74, 1993. Both ventricular fibrillation (VF) amplitude and frequency have therefore emerged as potentially promising real time and noninvasive measurements for guiding resuscitation interventions.

U.S. Pat. No. 5,077,667, issued Dec. 31, 1991, to Charles G. Brown and Roger Dzwonczyk entitled "Measurement of the Approximate Elapsed Time of Ventricular Fibrillation and Monitoring the Response of the Heart to Therapy" describes in detail a method for using the frequency of ventricular fibrillation (VF). The approximate elapsed time since the onset of VF is detected from an analog electrocardiogram signal. The signal is digitized for a time interval of four seconds to obtain a data set of time domain samples. These time domain samples are Fourier transformed to a frequency domain spectrum and the median frequency which bisects the energy of the power spectrum is detected. That median frequency is then compared to a pattern of experimentally obtained median frequency data as represented by a mathematical algorithm to calculate the estimated time from the onset of ventricular fibrillation. This frequency parameter can also be used to evaluate the response to therapy during ventricular fibrillation and CPR, as well as estimate the most appropriate time to defibrillate a subject following various pharmacologic and mechanical interventions.

U.S. Pat. Nos. 5,571,142 and 5,683,424, issued Nov. 5, 1996, and Nov. 4, 1997, respectively, also to Brown and Dzwonczyk, entitled "Non-invasive Monitoring and Treatment of Subjects in Cardiac Arrest Using ECG Parameters Predictive of Outcome" describe in detail methods and apparatus for determining the metabolic state of the myocardium of a subject in ventricular fibrillation or asystole and/or for guiding therapeutic interventions using the frequency of ventricular fibrillation (VF). Electrocardiographic signals of the subject are transformed to a frequency domain power spectrum, and at least one frequency parameter is monitored and processed to a value predictive of a clinically relevant cardiac arrest outcome. In the preferred embodiment, centroid frequency and/or peak power frequency of the power spectrum are monitored.

U.S. Pat. No. 5,643,325, issued Jul. 1, 1997, to Hrayr S. Karagueuzian, et al., entitled "Defibrillator with Shock Energy Based on EKG Transform" describes another method for using the frequency of ventricular fibrillation (VF). A phase-plane plot is made of a patient's electrocardiogram. The degree of deterministic chaos in the phase-plane plot is measured by a processor. Analysis of the phase-plane plot may indicate a propensity for fibrillation including both the risk of fibrillation and the actual onset of fibrillation. A second method for detecting a heart disorder comprises examination of a frequency domain transform developed by applying a fast Fourier transform to the EKG of a patient. An automatic defibrillating device delivers a shock which varies in size, at least in part, according to the peak energy disclosed by the fast Fourier transform.

Coronary perfusion pressure is the best single predictor of the success of cardiac resuscitation in animals, Ralston, S. H., et al., "Intrapulmonary Epinephrine During Prolonged Cardiopulmonary Resuscitation: Improved Regional Blood Flow and Resuscitation in Dogs," *Annals of Emergency Medicine,* 13:79–86, 1984; Halperin, H. R., et al., "Determinants of Blood Flow to Vital Organs During Cardiopulmonary Resuscitation in Dogs," *Circulation,* 73:539–550, 1986; and Wolfe, J. A., et al., "Physiologic Determinant of Coronary Blood Flow During External Cardiac Massage," *Journal of Thoracic Cardiovascular Surgery,* 95:523–532, 1988. Also, coronary perfusion pressure is the best single predictor in humans, Paradis, N. A., et al., "Coronary Perfusion Pressure and Return of Spontaneous Circulation in Human Cardiopulmonary Resuscitation," *JAMA—Journal of the American Medical Association,* 263:1106–1113, 1990. A threshold coronary perfusion pressure of 10 mm Hg is required in pigs for successful defibrillation and restoration of spontaneous circulation, Grundler, W., Weil, M. H., and Rackow, E. C., "Arteriovenous Carbon Dioxide and pH Gradients During Cardiac Arrest," *Circulation,* 74:1071–1074, 1986; Gudipati, C. V., Weil, M. H., Bisera, J., et al., "Expired Carbon Dioxide: a Noninvasive Monitor of Cardiopulmonary Resuscitation," *Circulation,* 77:234–239, 1988; and Gazmuri, R. J., von Planta, M., Weil, M. H. et al., "Cardiac Effects of Carbon Dioxide-consuming and Carbon Dioxide-generating Buffers During Cardiopulmonary Resuscitation," *Journal of the American College of Cardiology,* 5:482–490, 1990. A threshold coronary perfusion pressure of 15 mm Hg is required in humans for successful defibrillation and restoration of spontaneous circulation, Paradis, N. A., et al., supra.

However, there is currently no noninvasive or practical invasive option for measuring coronary perfusion pressure in or out of hospital settings. With the possible exception of end tidal $CO_2$, no practical alternative has been identified, Falk, J. L., Rackow, E. C., and Weil, M. H., "End-tidal Carbon Dioxide Concentration During Cardiopulmonary Resuscitation," *New England Journal of Medicine,* 318:607–611, 1988; and Sanders, A. B., et al., "End-tidal Carbon Dioxide Monitoring During Cardiopulmonary Resuscitation. A Prognostic Indicator for Survival," *JAMA,* 262:1347–1351. But these measurements require extensive instrumentation and sophistication ordinarily available only in experimental situations.

In view of the problems associated with measuring coronary perfusion pressure, electronic analysis of electrocardiographic ventricular fibrillation (VF) signals would appear to be more practical in most real world situations where the availability of specialized equipment is limited. The need for accurate electronic analysis has escalated since the introduction of automatic external defibrillators. Substantial hands-off intervals are mandated during which precordial compression is held in abeyance when the automatic external defibrillator cycles through electrocardiographic analysis, capacitor charge, and capacitor discharge. The process may be repeated for as many as three cycles and consume as long as 82 seconds. During such prolonged hands-off intervals, no cardiac output or coronary blood flow is generated by precordial compression. Such delays are likely to compromise the ultimate success of cardiopulmonary resuscitation and there is evidence of such based on recent studies on a murine model, Sato, Y., Weil, M. H., Sun, S., et al., "Time Limitations Between Stopping Precordial Compression and Defibrillation," *Critical Care Medicine,* 24 (1):A116 (abstract only), 1996.

DISCLOSURE OF INVENTION

The present invention is directed to an improved method and system for predicting the immediate success of a defibrillatory shock during cardiac arrest. The sequencing of cardiopulmonary resuscitation (CPR) or defibrillation is guided entirely by ventricular fibrillation wave analysis which focuses on the amplitude spectrum area (ASA) or the power spectrum area (PSA) of electrocardiogram (EKG) samples. After an EKG signal is acquired, an electronic computer selects at least one sample of the EKG signal and performs a frequency domain transform and other analyses to obtain either the ASA or PSA of the sample. The probability of successful defibrillation based on empirical data is determined and the probability is used to guide the course of action.

In accordance with a preferred embodiment of the invention, when the probability of successful (PS) resuscitation is 80% or greater, immediate defibrillation is advised. When PS is 20% or less, advanced cardiopulmonary resuscitation (CPR) is advised including precordial compression with or without fluids or drugs such as epinephrine. The EKG is continually monitored such as to detect a high (80%) likelihood of a shockable rhythm whereupon immediate electrical defibrillation is advised.

In accordance with an important aspect of the invention, in the intermediate range where PS is greater than 20% but less than 80%, advanced CPR is continued while the patient is monitored. Elective defibrillation may be selected at the option of the rescuer.

In accordance with an important feature of the invention, after four minutes of monitoring within the cautionary range between 20% and 80%, defibrillation is advised.

In accordance with an important aspect of the invention, a band pass filter is used to limit the frequency of the EKG sample to usable data within the range of 2 to 40 Hz.

In a preferred embodiment of the invention, the probability of defibrillation success is determined by the electronic computer solving a binary logistic regression model having a multiplicative constant and an additive constant.

In accordance with an important aspect of the invention, the ASA (area of the amplitude spectrum) is considered, the multiplicative constant is in the range from 0.20 to 0.40, and the additive constant is in the range from −4.00 to −9.00.

In accordance with an important feature of the invention where the ASA is the relevant factor, the multiplicative constant is substantially 0.32 and the additive constant is substantially −6.64.

On the other hand, when the area of the power spectrum is the factor under consideration, an important feature of the invention is that the multiplicative constant is in the range from 12.0 to 18.0, and the additive constant is in the range from −2.0 to −5.0.

In accordance with an important feature of the invention where the PSA is the relevant factor, the multiplicative constant is substantially 13.43 and the additive constant is substantially 3.85.

In accordance with an important aspect of the invention, the output of the electronic computer is coupled to a light display. When the probability of success (PS) is 80% or greater, a green light is activated. When PS is 20% or less, a red light is activated.

In accordance with an important feature of the invention where lights are displayed, a yellow light is activated by the computer when PS is less than 80% and greater than 20%.

In accordance with another important feature of the invention, if the system continues to sample the EKG signal for five minutes and the light remains yellow, the computer automatically changes the light to green indicating that the patient should be shocked.

In accordance with another important aspect of the invention, the results of the EKG monitoring allow for optional automatic activation of a defibrillator.

In accordance with another aspect of the invention, a PS (probability of success) calculating circuit and display are connected to an existing monitor/defibrillator.

Other features and advantages of the present invention will become apparent from the following detailed description, taken in conjunction with the accompanying drawings, which illustrate, by way of example, the principles of the invention.

MODES FOR CARRYING OUT THE INVENTION

Figure 1:
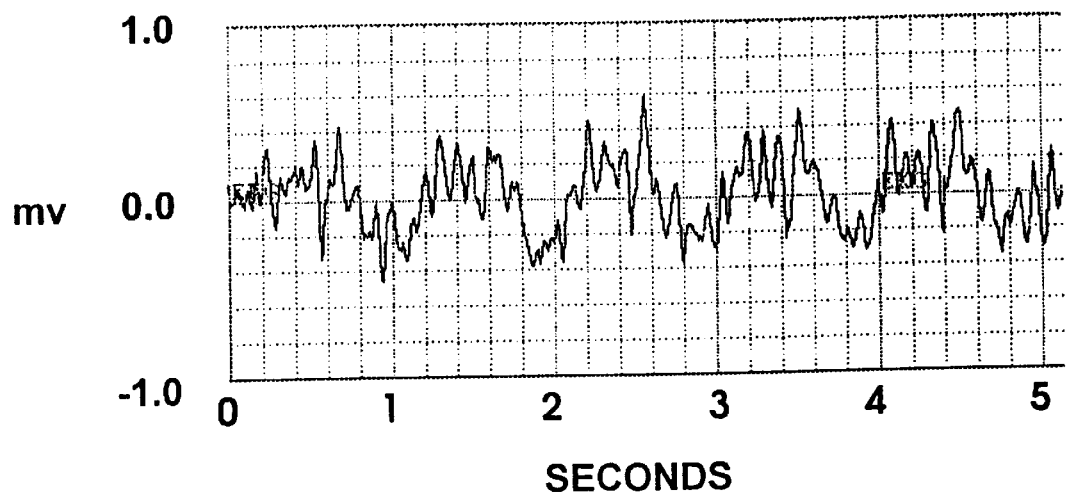
FIG. 1 is a typical chart of an EKG (electrocardiogram) of a heart demonstrating VF (ventricular fibrillation) being treated by closed chest CPR (cardiopulmonary resuscitation)

FIG. 1 shows a typical tracing of an electrocardiogram (EKG) demonstrating ventricular fibrillation (VF) during closed chest cardiopulmonary resuscitation (CPR). The EKG was recorded at 300 Hz by an AT Codas digital acquisition system. A time of 0 to 5 seconds is represented along the x-axis and a voltage range of −1 to +1 millivolts is represented along the y-axis. The waveform of FIG. 1 has two primary components. Three major waves having a period of approximately 1 second are associated with closed chest compression during cardiopulmonary resuscitation (CPR). The multiple small wavelets represent ventricular fibrillation.

The present invention is based on the morphology of such EKG waveforms for establishing optimal timing of electrical defibrillation. Electrical shocks always have adverse affects on the myocardium which are compounded when they are repetitive. Electrical defibrillation should therefore be used only when the benefits outweigh the harm. Optimally, only one shock will be delivered at the optimal time such as to successfully restart a regular heartbeat and blood circulation.

Figure 2:
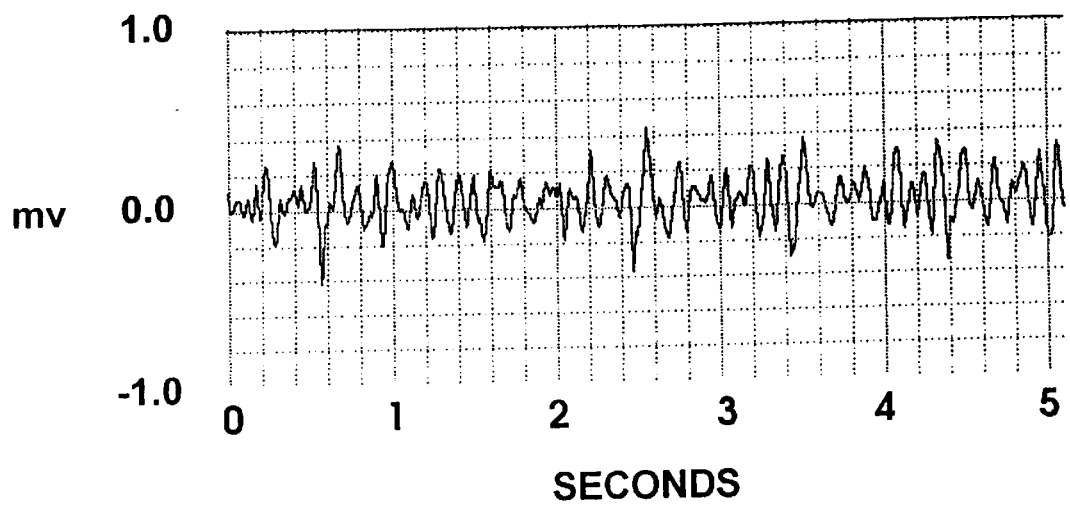
FIG. 2 shows the EKG signal of FIG. 1 after it is filtered to eliminate compression artifacts leaving only VF wavelets.

FIG. 2 shows the EKG signal of FIG. 1 after it is filtered to a range of 2 and 40 Hz by a band pass filter, primarily to eliminate the compression artifacts so as to leave only the VF wavelets. When compared to the EKG of a normal heart rhythm, the frequency and amplitude of the VF wavelets appear to be random. But they are not. They provide valuable information concerning the condition of the heart muscle and indicate the timing of electrical defibrillation to achieve successful optimal resuscitation.

In one study, cardiac arrest due to ventricular fibrillation was induced in 34 porcine subjects. Electrical defibrillation was attempted on 56 occasions immediately following onset of VF or at intervals after starting precordial compression. VF wavelets recorded in the 5 second interval immediately prior to attempted electrical defibrillation were analyzed. The statistical data cited below was abstracted from this study on 34 porcine subjects. While such subjects are not identical to humans, their heart morphology and function has long been recognized as closely related to that of humans and they are consequently often used for experimental heart studies. The numbers are similar to those which would be experienced in human studies. The numbers represent averages of all 34 porcine subjects.

One possible predictor of success in restoring spontaneous circulation by electrical defibrillation is the average peak-to-trough amplitude (AM) of the VF wavelet:

$$AM = \frac{\Sigma A_i}{N} \qquad \text{Equation 1}$$

where $A_i$ is the $i^{th}$ amplitude component and N is the number of amplitude components. In the present study, AM equaled 0.27 mv. In the prior art discussed above, significantly greater VF amplitudes have been associated with correspondingly greater likelihood of restoring spontaneous circulation.

Figure 3:
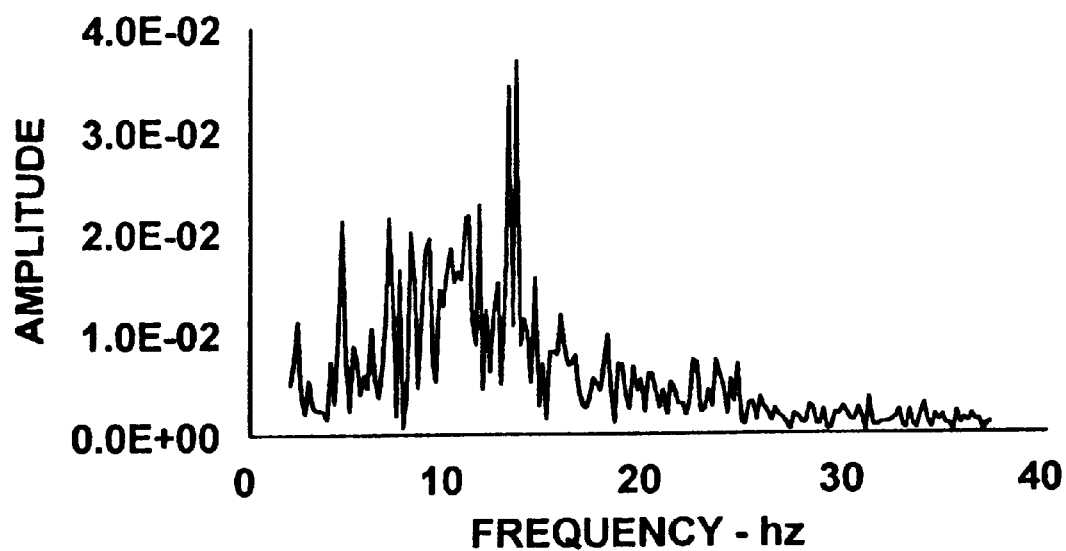
FIG. 3 is an amplitude spectrum of the VF wavelets of FIG. 2.

FIG. 3 is the amplitude spectrum of the VF wavelets of FIG. 2 with frequency plotted along the x-axis and amplitude plotted along the y-axis. Each time domain VF wavelet of FIG. 2 was transformed to the frequency domain using the fast fourier transform algorithm to obtain an amplitude spectrum as a series of sinusoidal components with corresponding magnitudes. Another possible predictor of success in restoring spontaneous circulation by electrical defibrillation is the area of the amplitude spectrum (ASA) shown in FIG. 3:

$$ASA = \Sigma A_i F_i, \qquad \text{Equation 2}$$

where $A_i$ is the amplitude at the $i^{th}$ frequency $F_i$. In the present study, ASA=15.4 mv·Hz.

Figure 4:
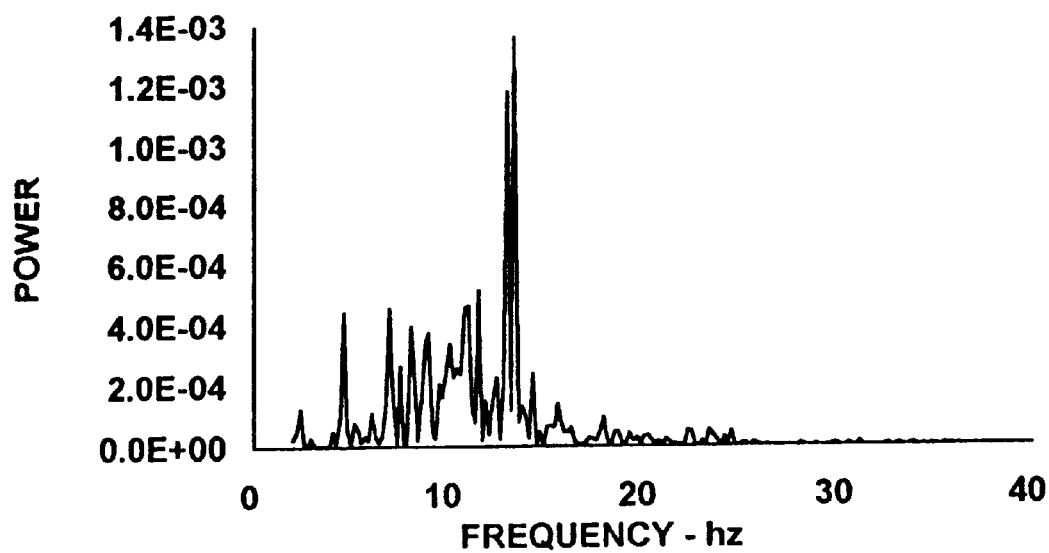
FIG. 4 is a power spectrum derived from FIG. 3.

FIG. 4 is a power spectrum derived from FIG. 3 created by squaring the amplitude of each sinusoidal component. Frequency is along the x-axis and power is along the y-axis. Another possible predictor of success in restoring spontaneous circulation by electrical defibrillation is the median frequency (MF) extracted from the power spectrum (ASA) shown in FIG. 4:

$$MF = \frac{\Sigma F_i \cdot P_i}{\Sigma P_i}, \quad \text{Equation 3}$$

where $F_i$ is the $i^{th}$ frequency component and $P_i$ is the relative power at $F_i$.

Another possible predictor of success in restoring spontaneous circulation by electrical defibrillation is the area of the power spectrum area (PSA) shown in FIG. 4:

$$PSA = \Sigma P_i F_i, \quad \text{Equation 4}$$

where $P_i$ is the power at the $i^{th}$ frequency $F_i$. In the present study, PSA=0.15 mv$^2$·Hz.

The purpose of the EKG signal analysis is to determine the parameter that will best predict the outcome of each episode of electrical defibrillation independent of any clinical variable. Since the outcome variable is dichotomous, i.e., resuscitated or non-resuscitated, the data may be analyzed utilizing a logistic regression model. The method of regression analysis is described in *Modern Regression Methods*, by Thomas P. Ryan, © 1996, John Wiley & Sons, Inc., New York, N.Y. The following table shows the relationship between parameters involved when AM (peak-to-trough amplitude of VF wavelets), ASA (amplitude spectrum of VF wavelets), MF (median frequency of VF wavelets), or PSA (power spectrum of VF wavelets) is used to calculate probability:

| Predictor | Logistic coefficient (b) | Standard Error (SE) | Ratio | P | NLL |
|---|---|---|---|---|---|
| AM | 13.90 | 5.00 | 2.76 | 0.008 | 48.2 |
| ASA | 0.27 | 0.07 | 3.42 | 0.001 | 37.8 |
| MF | 0.14 | 0.10 | 1.40 | 0.16 | 60.9 |
| PSA | 10.25 | 3.41 | 3.00 | 0.004 | 42.6 |

AM, ASA, and PSA are highly correlated with successful resuscitation by defibrillation as shown by the negative log likelihood (NLL) value which measures the lack of fit between the data and the model such that the smaller the NLL value, the better the model fits the data. Since the predictor ASA (amplitude spectrum area) has the lowest NLL value, it is the best predictor of successful resuscitation. The next best predictor is PSA (power spectrum area). The next step is to determine at what levels of ASA or PSA one or more defibrillation shocks should be delivered or disadvised because the harm caused by the electrical shock outweighs the possible benefit, and also indicate at what levels of ASA or PSA the benefits of defibrillation are questionable. To establish a threshold level at which the probability of resuscitation is favorable, the binary logistic regression model is used to assess the relation between the outcome and the EKG characteristics:

$$PS = \frac{e^{(ax+b)}}{1 + e^{(ax+b)}}, \quad \text{Equation 5}$$

where PS represents the probability of success, x=measured variable, "a" is a multiplicative constant and "b" is an additive constant derived from empirical data that provide the best fit.

When empirical ASA values are used to determine the predicted outcome, the equation preferably becomes:

$$PS = \frac{e^{(0.32 \cdot ASA - 6.64)}}{1 + e^{(0.32 \cdot ASA - 6.64)}} \quad \text{Equation 6}$$

However, the multiplicative constant may range from 0.20 to 0.40 and the additive constant may range from −4.00 to −9.00 depending upon the subjects. For a person, the constants are about as shown in Equation 6.

One example is taken from FIG. 3 where the area under the graph of amplitude vs. frequency (ASA) between 2 and 40 Hz is 15.4 mv·Hz (above 37 Hz the amplitude is substantially zero). Using this area, the PS (probability of survival) is calculated as follows:

$$PS = \frac{e^{(0.32 \cdot 15.4 - 6.64)}}{1 + e^{(0.32 \cdot 15.4 - 6.64)}} = 0.15 \quad \text{Equation 7}$$

In FIG. 4, the area under the graph of power vs. frequency is 0.15 milliwatt·Hz. When entered into Equation 8 below, this yields a PS of 0.14.

Figure 5:
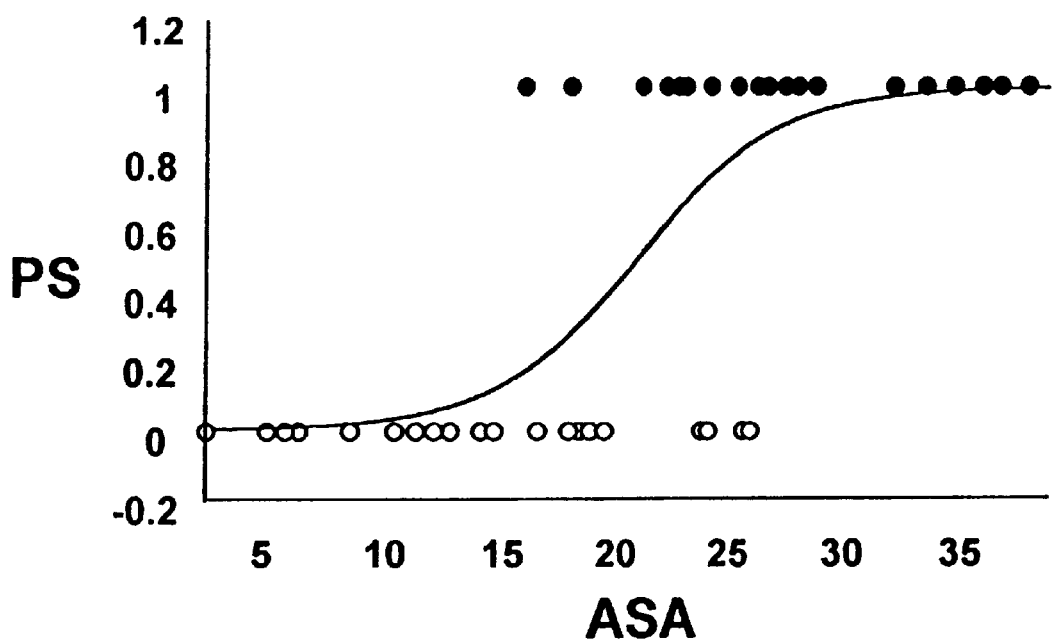
FIG. 5 is a graph of the results of a porcine study for ASA (area of amplitude spectrum)

FIG. 5 is a graph of the empirical results from the study of porcine subjects with the ASA values for each subject represented along the x-axis and the PS (probability of success) values represented along the y-axis. Only two results are possible: 1 for successful resuscitation or 0 for non-resuscitation. The cumulative probability of success is shown by the curved line. Until an ASA of 16 was reached, no defibrillations were successful. After an ASA of 27 is reached, all defibrillations were successful. When ASA=20.7, PS=0.5 or 50% meaning that there is equal likelihood that defibrillation may or may not be successful. Likewise, at ASA=25, PS=0.80 indicating an 80% chance of successful defibrillation and at ASA=16, PS=0.20 indicating only a 20% chance of successful defibrillation.

When empirical PSA values are used to determine the predicted outcome, the equation preferably becomes:

$$PS = \frac{e^{(13.43 \cdot PSA - 3.85)}}{1 + e^{(13.43 \cdot PSA - 3.85)}} \quad \text{Equation 8}$$

Figure 6:
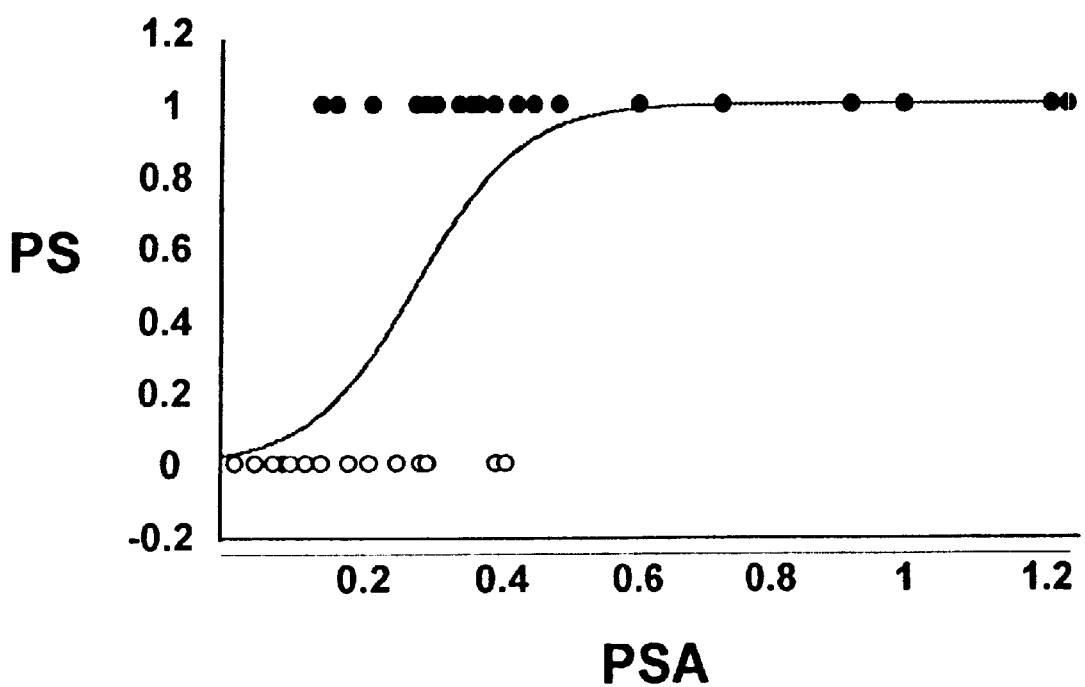
FIG. 6 is a graph of the results of a porcine study for PSA (area of power spectrum)

However, the multiplicative constant may range from 12.0 to 18.0 and the additive constant may range from −2.0 to −5.0 depending on the subjects. FIG. 6 is a graph of the empirical results from the study of porcine subjects with the PSA values for each subject represented along the x-axis and the PS (probability of success) values represented along the y-axis. Again, only two results are possible: 1 for successful resuscitation or 0 for non-resuscitation. The cumulative probability of success is shown by the curved line. Until a PSA of 0.2 was reached, no defibrillations were successful. After a PSA of 0.43 was reached, all defibrillations were successful. When PSA=0.28, PS=0.5 or 50% meaning that there is equal likelihood that defibrillation may or may not be successful. Likewise, at PSA=0.39, PS=0.80 indicating a 80% chance of successful defibrillation and at PSA=0.19, PS=0.20 indicating only a 20% chance of successful defibrillation.

Figure 7:
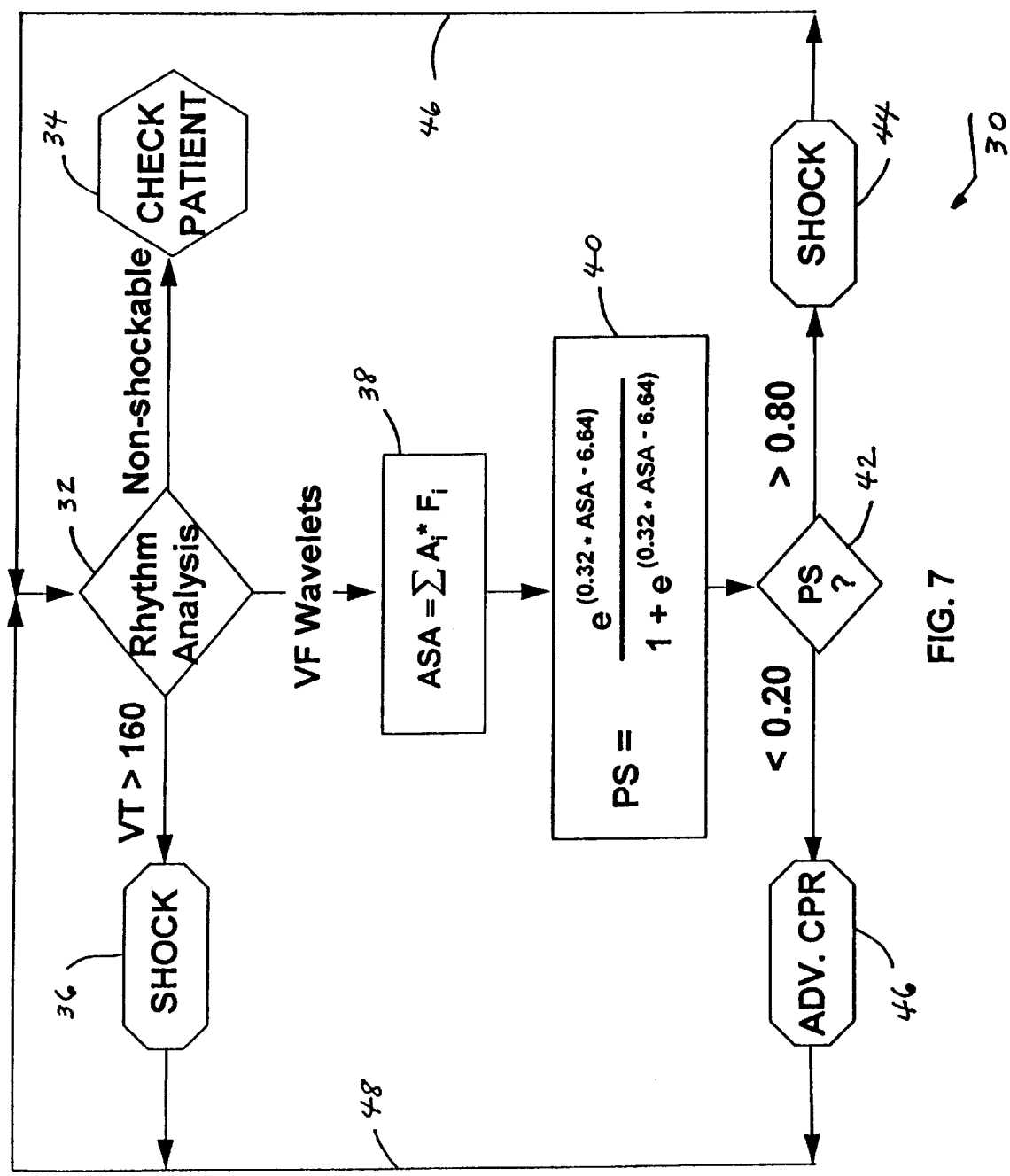
FIG. 7 is a flow chart showing the procedure for guiding the sequencing of electrical defibrillation based on ASA in accordance with the present invention.

FIG. 7 is a flow chart showing the procedure for guiding the sequencing of electrical defibrillation, generally designated 30, in accordance with the present invention based on the results of the above studies concerning ASA (amplitude spectrum area). After an EKG lead is attached to the patient, a decision 32 is made regarding the heart rhythm. If a regular pulse is detected, the patient is not shocked, the procedure is stopped 34, and the patient is checked for other conditions. If a regular pulse is not present but ventricular tachycardia (VT) is detected having more than 160 pulses per minute, the patient is shocked 36 immediately in an attempt to restore a regular heartbeat. VT is a condition where the patient is clinically in cardiac arrest but still has some degree of myocardial perfusion.

If ventricular fibrillation (VF) is detected, the VF wavelets are analyzed 38 in accordance with the procedure given above to determine the ASA (amplitude spectrum area). After the ASA is determined, the result is interpreted 40 in accordance with the procedure given above to determine the probability of resuscitation at the identified ASA level. A decision 42 is then made whether to shock the patient or not shock the patient. Since the intent is to maximize the probability of successful resuscitation (PS) by defibrillation while minimizing damage to the myocardium, a value of PS>0.80 is chosen as a guideline for shocking 44 the patient. After shocking, the sequence loops around 46 immediately to determine the result on the patient. If resuscitation was successful, the sequence stops 34. If resuscitation was not successful, the sequence continues.

Alternatively, a value of PS<0.20 is chosen as a threshold below which advanced CPR 46 including precordial compression and fluid and/or drug therapy is always used. As the advanced CPR 46 continues, the sequence loops around 48 continuously to determine the status of the patient should any changes occur warranting the stopping of advanced CPR or shocking.

In the range where PS is between 0.20 and 0.80, advanced CPR is performed and shocks are administered at the discretion of the physician. Should PS remain between 0.20 and 0.80 for a minimum of 2 to 4 minutes, the patient is shocked.

Figure 8:
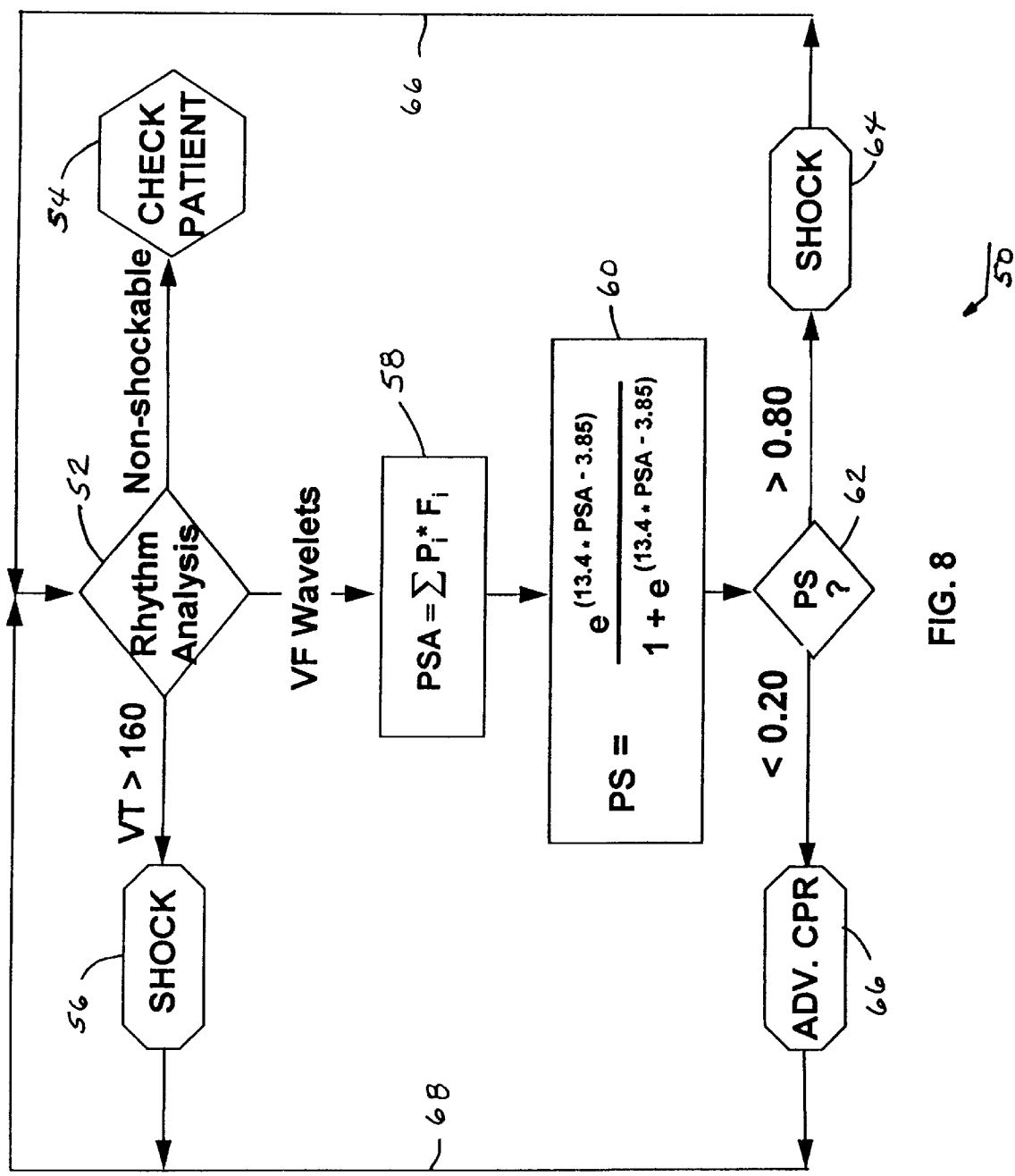
FIG. 8 is a flow chart showing the procedure for guiding the sequencing of electrical defibrillation based on PSA in accordance with the present invention.

FIG. 8 is a flow chart showing the procedure for guiding the sequencing of electrical defibrillation, generally designated 50, in accordance with the present invention based on the results of the above studies concerning PSA (power spectrum area). The procedure is identical for that used in conjunction with ASA except the formulas used are the ones for PSA. After an EKG is attached to the patient, a decision 52 is made regarding the heart rhythm. If a regular pulse is detected, the procedure is stopped 54. If a regular pulse is not present but VT (ventricular tachycardia) is detected having more than 160 pulses per minute, the patient is shocked 56 immediately. If VF is detected, the VF wavelets are analyzed 58 in accordance with the procedure given above to determine the PSA. After PSA is determined, the result are interpreted 60 in accordance with the procedure given above to determine the probability of resuscitation at the identified PSA level. A decision 62 is then made whether to shock the patient or not shock the patient. A value of PS>0.80 is chosen as a guideline for shocking 64 the patient. After shocking, the sequence loops around 66 immediately to determine the result on the patient. A value of PS<0.20 is chosen as a threshold below which advanced CPR 66 including precordial compression and fluid and/or drug therapy is always used. As the advanced CPR 66 continues, the sequence loops around 68 continuously to determine the status of the patient should any changes occur warranting the stopping of advanced CPR or shocking. In the range where PS is between 0.20 and 0.80, advanced CPR is performed and shocks are administered at the discretion of the physician. Should PS remain between 0.20 and 0.80 for a minimum of 2 to 4 minutes, the patient is shocked. The levels of about 80% (preferably 70% to 90% and more preferably 75% to 85%) and about 20% (preferably 10% to 30% and more preferably 15% to 25%) are good predictors of when defibrillation is definitely useful and definitely not useful.

Figure 9:
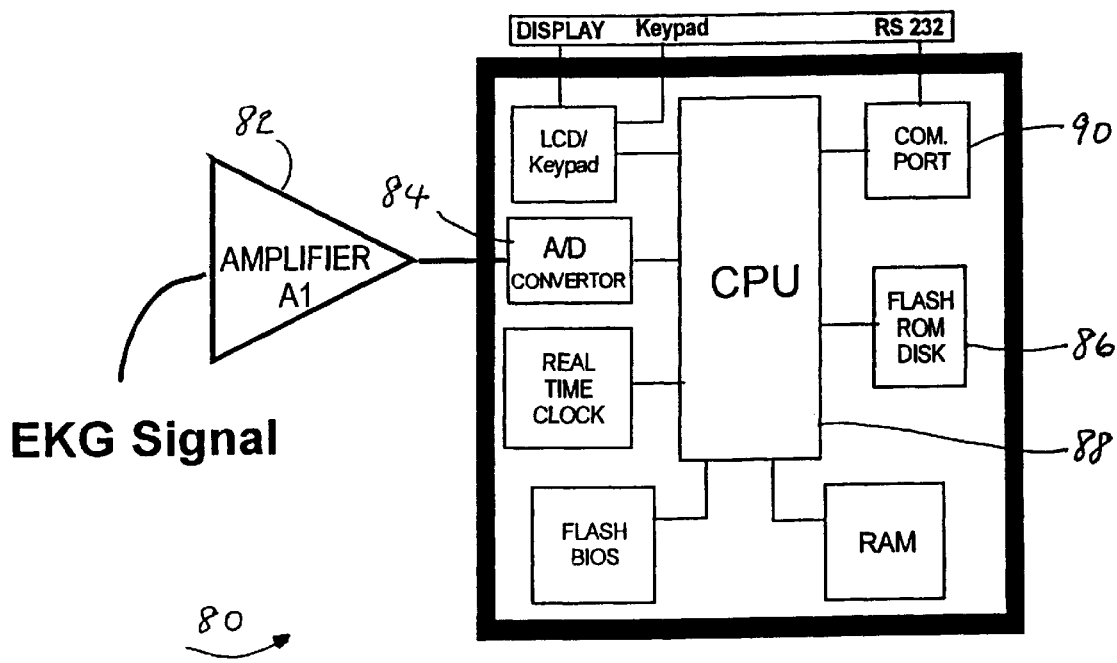
FIG. 9 is a block diagram of a computer for processing the EKG signal in accordance with the present invention; and, FIG. 10 is front top perspective view of a display for visually representing the output of the computer of FIG. 9.
Figure 10:
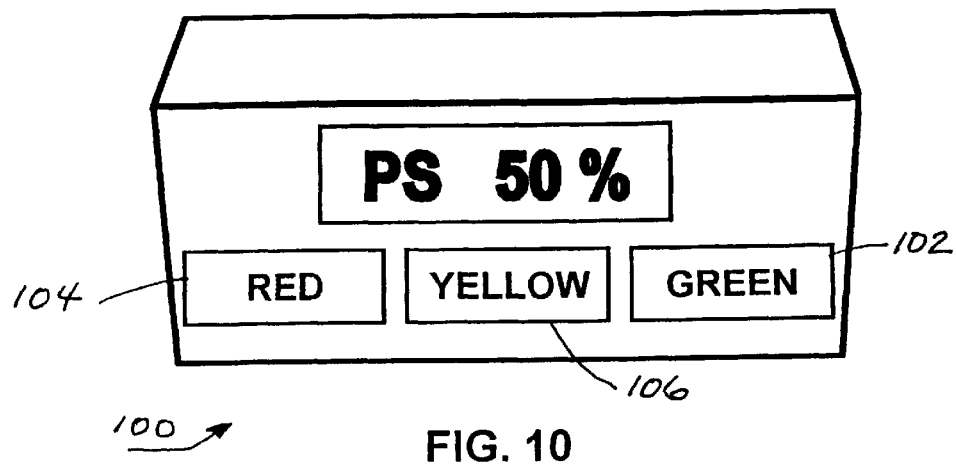

FIG. 9 is a block diagram of a single board computer data acquisition system 80 which can be added to an existing EKG monitor/defibrillator for processing the EKG signal in accordance with the flow charts of FIGS. 7 and 8. An amplifier 82 buffers the analog signals such as those shown in FIG. 1 as they arrive from the EKG, and a 2 to 40 Hz band pass filter removes undesired artifacts especially those resulting from precordial compression. This results in the amplifier 82 producing a signal such as shown in FIG. 2. An analog to digital converter 84 converts the signal to a digital signal for analysis by the system 80. The program for analyzing the EKG signals resides on a FLASH ROM DISK 86 and is transferred to the central processing unit (CPU) 88 for use. Sets of VF wavelets having a duration of 3 to 5 seconds are analyzed. The samples are preferably taken before any shock is administered. Each time domain set of VF wavelets is transformed to a frequency domain using the fast fourier transform algorithm to obtain an amplitude spectrum for the subject set similar to the one shown in FIG. 3. The area of the amplitude spectrum (ASA) and the probability of a successful resuscitation are computed in accordance with the formulas given in conjunction with the discussion of FIG. 3. If a probability of 80% or greater is indicated, a signal is sent through the communications port 90 to an output device such as the visual output device 100 shown in FIG. 10. Visual output device 100 has a green light 102 which lights in response to the signal telling the operator that it is permissible to defibrillate the patient. If a probability of 20% or less is indicated, a signal is sent to the visual output device 100 to light a red light 104 advising the operator not to shock the patient and proceed with alternative therapy such as advanced CPR including precordial compression and drugs. If a probability between 20% and 80% is indicated, a signal is sent to the visual output device 100 to light a yellow light 106 advising the operator to proceed with caution. After 4 minutes of continuous yellow conditions, a signal is given by the system 100 advising an electrical shock.

Alternatively, the output from the communications port 90 can be used to directly control an automatic defibrillator or as an interface to bedside electronic systems or remote displays/alarms.

The process is similar if PSA (power spectrum area) is used instead of ASA (amplitude spectrum area). The procedure described in conjunction with FIG. 8 is used instead. The output is them fed to the visual output device 100 with the lights 102, 104, and 106 being lighted according to the computed probabilities of successful resuscitation.

The preferred embodiments of the invention described herein are exemplary and numerous modifications, dimensional variations, and rearrangements can be readily envisioned to achieve an equivalent result, all of which are intended to be embraced within the scope of the appended claims.

We claim:

1. A system for guiding the sequencing of cardiopulmonary resuscitation, comprising:

means for acquiring an EKG signal;

means for selecting at least one sample of said EKG signal;
  means for performing a frequency domain transform of said at least one sample and for obtaining an amplitude spectrum of said transform of said sample;
  means for computing the area of said amplitude spectrum; and,
  means for using the computation of the area of said amplitude spectrum to determine whether or not to provide a defibrillatory shock.

2. A system for guiding the sequencing of cardiopulmonary resuscitation, comprising:
  means for acquiring an EKG signal;
  means for selecting at least one sample of said EKG signal;
  means for performing a frequency domain transform of said at least one sample and for obtaining a power spectrum;
  means for computing the area of said power spectrum; and,
  means for using the computation of the area of said power spectrum to determine whether or not to provide a defibrillatory shock.

\* \* \* \* \*